United States Patent [19]

Walton et al.

[11] 3,981,918

[45] Sept. 21, 1976

[54] ISOPHORONE PRODUCTION USING A POTASSIUM HYDROXIDE CATALYST

[75] Inventors: John Reginald Walton, Hull; Bertram Yeomans, Hessle, both of England

[73] Assignee: BP Chemicals International Limited, London, England

[22] Filed: Apr. 21, 1975

[21] Appl. No.: 570,175

[30] Foreign Application Priority Data

May 15, 1974 United Kingdom............... 21651/74

[52] U.S. Cl............................................. 260/586 C
[51] Int. Cl.$^2$...................................... C07C 45/00
[58] Field of Search............................. 260/586 C

[56] References Cited
UNITED STATES PATENTS

| | | | |
|---|---|---|---|
| 2,434,631 | 1/1948 | Winkler et al. | 260/586 C |
| 3,337,423 | 8/1967 | Schmitt et al. | 260/586 C |
| 3,337,632 | 8/1967 | Schmitt et al. | 260/586 C |
| 3,337,633 | 8/1967 | Schmitt et al. | 260/586 C |
| 3,462,348 | 8/1969 | Wellman et al. | 260/586 C |

FOREIGN PATENTS OR APPLICATIONS

| | | | |
|---|---|---|---|
| 603,810 | 6/1948 | United Kingdom | 260/586 C |
| 886,931 | 1/1962 | United Kingdom | 260/586 C |

*Primary Examiner*—Norman Morgenstern
*Attorney, Agent, or Firm*—Brooks Haidt Haffner & Delahunty

[57] ABSTRACT

Isophorone is produced by feeding a mixture comprising 65 to 85% w/w acetone, 35 to 15% w/w water and 0.7 to 0.3% w/w potassium hydroxide to an intermediate point in a reaction column, operating at elevated pressure, at such a rate as to maintain an acetone/water azeotrope reflux having a potassium hydroxide concentration in the range 300 to 1000 ppm within the reaction column, passing from the bottom of the column a fraction containing isophorone to a hydrolysis column also operating at elevated pressure wherein acetone is separated overhead and returned to the reaction column, removing the fraction containing water, isophorone and high-boiling compounds from the bottom of the hydrolysis column, and thereafter recovering the isophorone from the bottom fraction.

3 Claims, 1 Drawing Figure

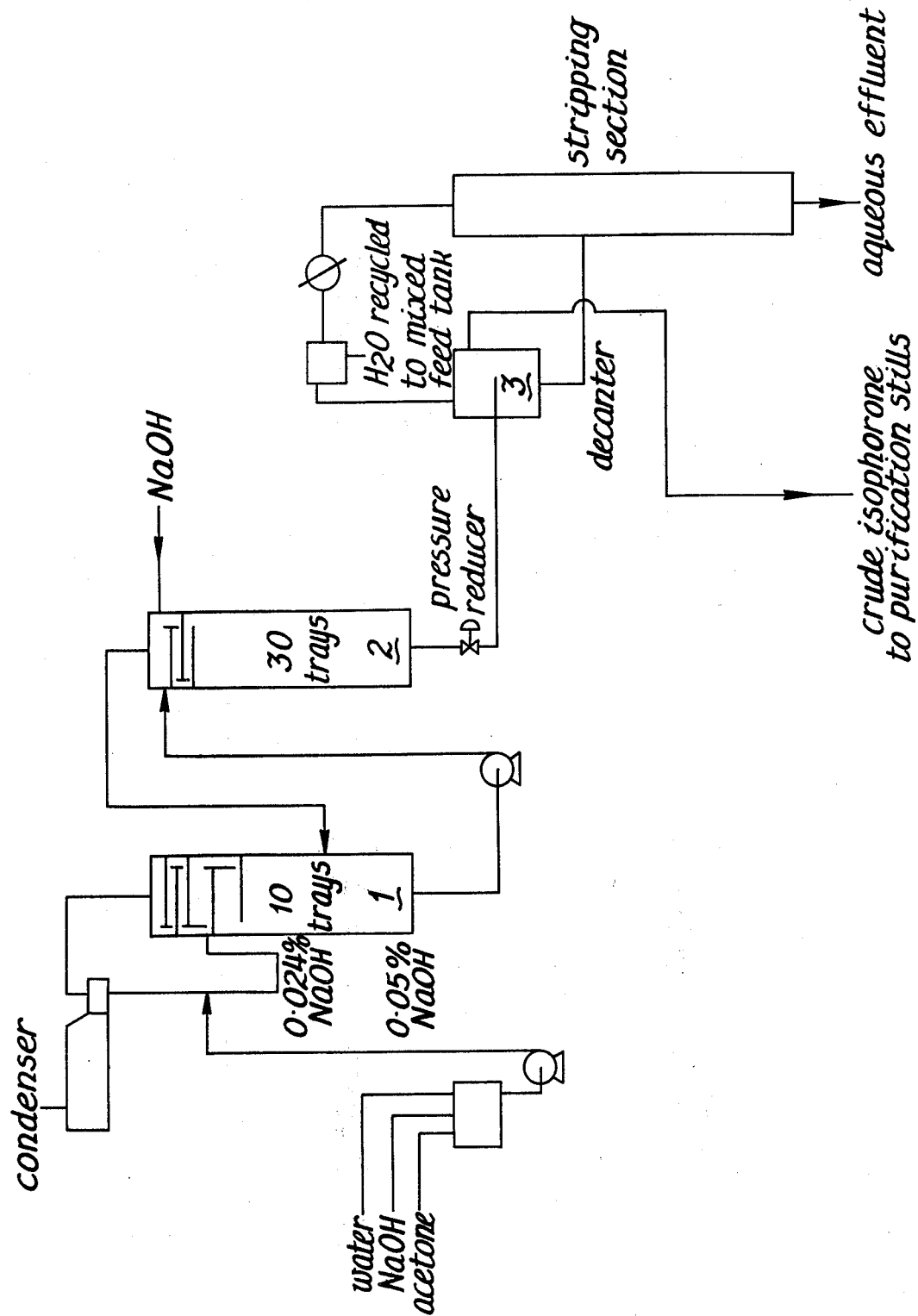

ISOPHORONE PRODUCTION USING A POTASSIUM HYDROXIDE CATALYST

The present invention relates to a method for the production of isophorone.

Isophorone is produced by the alkali catalysed condensation of acetone at high pressure. In a commercial process a feedstock consisting of water, acetone and sodium hydroxide is fed to a high pressure reaction column containing a refluxing azeotropic mixture of acetone and water. The acetone is converted to isophorone and high-boiling by-products which pass down the reaction column in the descending reflux and enter a second column, a hydrolysis column, in which unconverted acetone is stripped from the crude isophorone and recycled as a vapour to the reaction column. In the hydrolysis column a small amount of isoxylitone co-produced with the isophorone is hydrolysed back to isophorone and acetone. The crude isophorone product leaving the hydrolysis column is decanted from a water phase and purified by topping free from water and by tailing from the high-boilers in two vacuum stills.

The conversion to isophorone is dependent on catalyst concentration and increases in the conversion to isophorone are usually accompanied by increases in the conversion to higher boiling by-products thereby reducing the selectivity to isophorone. The production of isophorone is therefore dependent on the catalyst concentration.

It has now been surprisingly found that increased production of isophorone can be achieved under certain circumstances without a substantial loss in selectivity using a potassium hydroxide catalyst.

Thus according to the present invention there is provided a process for the production of isophorone which process comprises feeding a mixture comprising 65 to 85% w/w acetone, 35 to 15% w/w water and 0.7 to 0.3% w/w potassium hydroxide to an intermediate point in a reaction column, operating at elevated temperature and pressure, at such a rate as to maintain an acetone/water azeotrope reflux having a potassium hydroxide concentration in the range 300 to 1000 ppm within the reaction column, transferring from the bottom of the column a fraction containing isophorone to a hydrolysis column also operating at elevated temperature and pressure wherein acetone is separated overhead and returned to the reaction column, removing the fraction containing water, isophorone and high-boiling compounds from the bottom of the hydrolysis column and thereafter recovering the isophorone from the bottom fraction.

Whilst the reaction column and the hydrolysis column may be operated as separate columns it is preferred that they are integrated as separate sections within the same column, the rectification section of the column acting as the reaction column and the stripping section of the column acting as the hydrolysis column.

The temperature in both the reaction column and hydrolysis column may suitably be in the range 150° to 250°C and the pressure may suitably be in the range 10 to 55 bar. The residence time in the reaction column may be in the range 20 to 120 minutes.

The acetone/water azeotrope reflux in the reaction column typically has a composition of approximately 80% w/w acetone and 20% w/w water at about 250°C and 32 bar pressure. It is preferred to operate the column under conditions which maintain not less than 20% water in the acetone/water azeotrope reflux.

Whether the reaction column and the hydrolysis column are separate columns or are integrated within a single column, heat may be supplied in the form of live steam or by a heat exchanger using any conducting medium such as oil or by any other method known in the art. When heating is effected by the injection of live steam additional water is introduced into the reaction column by condensation of the steam. Furthermore the condensation of acetone itself results in water formation. Both these sources of water supplement the water introduced in the feedstock in maintaining the acetone/water azeotrope reflux. However when heating is effected by methods other than the injection of live steam it is advisable and even when live steam is injected it is preferred, to feed a mixture comprising 65 to 75% w/w acetone, 35 to 25% w/w water and 0.7 to 0.3% w/w potassium hydroxide in order to maintain the acetone/water azeotrope reflux in the reaction column.

Preferably the feed mixture is fed to an intermediate point in the reaction column at such a rate as to maintain a potassium hydroxide concentration in the range 480 to 800 ppm in the reaction column reflux.

Whilst further potassium hydroxide may be added to the hydrolysis column it is preferred not to make any such further addition. In the hydrolysis column higher boiling products formed by side-reactions in the reaction column are hydrolysed. For example xylitone, one of the by-products, is hydrolysed to isophorone and acetone.

The isophorone may be recovered from the fraction removed from the bottom of the hydrolysis column by separating off the bulk of the water, feeding the isophorone phase to a distillation column wherein the last traces of water are removed and passing the bottoms fraction comprising isophorone and high-boiling compounds to a further distillation column from which pure isophorone is separated as an overhead fraction.

The bulk of the water is preferably separated from the fraction removed from the bottom of the hydrolysis column by decantation of the aqueous phase. It is preferred to add potassium hydroxide in an amount sufficient to make the total concentration about 0.7% w/w in order to aid phase separation during decantation.

Isophorone is useful as a high boiling solvent for surface coatings, printing inks, polyvinyl chloride processing and as a pesticide. It is a chemical intermediate in the production of a polyamide and a phenol, 3,5-xylenol.

The invention will now be illustrated by the following Examples:

EXAMPLE 1

Conventional Operation with NaOH catalyst

The procedure will be described with reference to the Drawing which is a flow-diagram showing the plant used.

A feed mixture comprising about 60% w/w acetone, 38.8% w/w ester and 0.2% w/w NaOH was fed on to the 7th plate of a 10-plate bubble cap reaction column 1 containing a refluxing azeotropic mixture of acetone and water (ca. 80:20 w/w) at ca. 205°C/32 bar. Under steady conditions a concentration of 240 ppm NaOH was obtained in the reflux below the 7th plate. The acetone was converted to isophorone and by-products which passed down the reaction column in the descending reflux into the hydrolysis column 2 (containing 30 bubblecap plates) where the unconverted acetone was stripped from the isophorone and recycled as a vapour to the reaction column 1. Concentrated aqueous NaOH (10% w/w) was fed to the top of the hydrolysis column 2. A small amount of isoxylitone present in the isophorone was hydrolysed back to isophorone and acetone in the hydrolysis column 2. The crude isophorone product leaving the hydrolysis column 2 was decanted from the water phase in the decanter 3 and further purified by topping free from water and by tailing from the high boilers in two vacuum stills (not shown).

The rate of addition of the acetone feed mixture to the reaction still 1 was increased until the hydrolysis column 2 was loaded to the flood point with recycling acetone. This caused carry over of NaOH from the hydrolysis column into the bottom of the reaction column thus increasing the concentration of NaOH from ca. 240 to 520 ppm in the reaction product. The rate of production of isophorone obtained under these conditions was concluded to be the maximum. A 5.9% w/w conversion of acetone to isophorone was thus obtained in 85.2% selectivity together with 12.5% selectivity loss to high boilers.

This Example is not an Example according to the invention and is included only for comparison purposes.

Operation with KOH catalyst

EXAMPLE 2

The procedure used in Example 1 was repeated using the same feed rate and apparatus for a mixture comprising 65% w/w acetone, 34.7% w/w water and 0.3% w/w KOH. Under steady conditions, 385 ppm of KOH (equivalent to 275 ppm NaOH) was present in the reflux below the 7th plate of the reaction column 1. The same concentration of caustic was also obtained at the bottom of the reaction column showing that the conversion to isophorone had been increased (from 5.9 to 7.4% w/w) thus reducing the amount of recycle acetone in the two high pressure columns. Under these conditions the rate of production of isophorone was increased to 107% of the previously assumed maximum without apparently adversely affecting the selectivity to isophorone and high boilers (85.9% and 11.8% respectively).

EXAMPLE 3

The procedure used in Example 1 was repeated again, increasing the feed rate to ca. 130% of that used in Example 1, with a feed mixture comprising 71% w/w acetone, 28.6% w/w water and 0.4% w/w KOH. 520 ppm of KOH was present in the reflux below the 7th plate of the reaction column and 10.4% w/w conversion of acetone to isophorone was obtained in the reaction product. The rate of production of isophorone was thus increased to ca. 140% of the previously assumed maximum for a slight decrease in selectivity to isophorone (to 82%) and a slightly increased selectivity loss to high boilers (to 16.2%). This result shows that the rate of production of isophorone can be substantially increased by using KOH catalyst for only a small loss in selectivity (3%) which is relatively far lower than that calculated on a 'pro-rata' basis (9.5%).

We claim:

1. A process for the production of isophorone by feeding a mixture of acetone, water and an alkali to an intermediate point in a reaction column operating at elevated temperature and pressure and under an acetone/water azeotrope reflux, passing from the bottom of said column a fraction containing isophorone to a hydrolysis column also operating at elevated temperature and pressure wherein acetone is separated overhead and returned to said reaction column and a fraction containing water, isophorone and high-boiling compounds is removed from the bottom of said hydrolysis column and thereafter isophorone is recovered from said bottom fraction wherein the invention comprises feeding a mixture consisting of 65 to 85% w/w acetone, 35 to 15% w/w water and 0.7 to 0.3% w/w potassium hydroxide to said intermediate point in said reaction column at such a rate as to maintain an acetone/water azeotrope reflux having a potassium hydroxide concentration in the range 300 to 1000 ppm within said reaction column.

2. A process according to claim 1 wherein a mixture consisting of 65 to 75% w/w acetone, 35 to 25% w/w water and 0.7 to 0.3% w/w potassium hydroxide is fed to said intermediate point in said reaction column.

3. A process according to claim 2 wherein said mixture is fed to said intermediate point in said reaction column at such a rate as to maintain an acetone/water azeotrope reflux having a potassium hydroxide concentration in the range 480 to 800 ppm.

* * * * *